(12) United States Patent
Bothma

(10) Patent No.: US 9,387,298 B2
(45) Date of Patent: Jul. 12, 2016

(54) FAN UNIT WITH IMPROVED SURGE CHARACTERISTICS

(75) Inventor: Johannes Nicolaas Bothma, Otorohanga (NZ)

(73) Assignee: FISHER & PAYKEL HEALTHCARE LIMITED, Auckland (NZ)

( * ) Notice: Subject to any disclaimer, the term of this patent is extended or adjusted under 35 U.S.C. 154(b) by 1200 days.

(21) Appl. No.: 13/318,112

(22) PCT Filed: Apr. 29, 2010

(86) PCT No.: PCT/NZ2010/000083
§ 371 (c)(1),
(2), (4) Date: Nov. 22, 2011

(87) PCT Pub. No.: WO2010/126383
PCT Pub. Date: Nov. 4, 2010

(65) Prior Publication Data
US 2012/0067347 A1 Mar. 22, 2012

Related U.S. Application Data

(60) Provisional application No. 61/173,656, filed on Apr. 29, 2009.

(51) Int. Cl.
*F04D 29/44* (2006.01)
*A61M 16/00* (2006.01)
*A61M 16/16* (2006.01)
*F04D 29/42* (2006.01)
*A61M 16/10* (2006.01)

(52) U.S. Cl.
CPC ....... *A61M 16/0066* (2013.01); *A61M 16/0069* (2014.02); *A61M 16/109* (2014.02); *A61M 16/1095* (2014.02); *A61M 16/16* (2013.01); *F04D 29/4233* (2013.01); *F04D 29/441* (2013.01)

(58) Field of Classification Search
CPC ............... A61M 16/0066; A61M 16/0063; A61M 16/0069; A62B 18/045; A62B 18/006; F04D 1/00–1/14; F04D 17/08; F04D 29/441–29/444; F04D 29/423
See application file for complete search history.

(56) References Cited

U.S. PATENT DOCUMENTS 4,111,615 A * 9/1978 Watanabe ................. 417/423.2
4,770,605 A * 9/1988 Nakatomi .................... 415/148
5,352,089 A * 10/1994 Tokunaga et al. ............. 415/206

(Continued)

FOREIGN PATENT DOCUMENTS

GB 932386 A 7/1963
JP 60-129000 7/1985

(Continued)

OTHER PUBLICATIONS

International Search Report; dated Sep. 8, 2010, 4 pages.

(Continued)

*Primary Examiner* — Valerie L Woodward
(74) *Attorney, Agent, or Firm* — Knobbe Martens Olson & Bear LLP

(57) ABSTRACT

A fan unit that forms part of a gases supply unit used as part of a breathing assistance system for providing heated gases to a user. The fan has an impeller surrounded by an upwardly sloped surface to facilitate improved airflow performance under surge conditions.

38 Claims, 13 Drawing Sheets

(56) References Cited

U.S. PATENT DOCUMENTS

| | | | |
|---|---|---|---|
| 6,171,078 B1 * | 1/2001 | Schob | 417/423.1 |
| 6,302,105 B1 * | 10/2001 | Wickham et al. | 128/204.18 |
| 6,302,661 B1 * | 10/2001 | Khanwilkar et al. | 417/423.7 |
| 6,881,033 B2 * | 4/2005 | Makinson et al. | 416/3 |
| 7,866,944 B2 * | 1/2011 | Kenyon et al. | 415/199.2 |
| 8,272,837 B2 * | 9/2012 | Kenyon et al. | 415/199.2 |
| 2002/0000228 A1 * | 1/2002 | Schoeb | 128/204.19 |
| 2003/0235497 A1 * | 12/2003 | Meng | 415/208.3 |
| 2004/0000310 A1 | 1/2004 | Wickham et al. | |
| 2008/0072900 A1 * | 3/2008 | Kenyon | A61M 16/0051 128/204.18 |

FOREIGN PATENT DOCUMENTS

| | | |
|---|---|---|
| JP | 61-004898 A | 1/1986 |
| JP | 61-028800 A | 2/1986 |
| JP | 01-295000 | 11/1989 |
| WO | WO 2007/134405 A1 | 11/2007 |

OTHER PUBLICATIONS

Written Opinion of the International Searching Authority; Sep. 8, 2010, 6 pages.

* cited by examiner

FAN UNIT WITH IMPROVED SURGE CHARACTERISTICS

CROSS-REFERENCE TO RELATED APPLICATIONS

This application is the national phase of International Application No. PCT/NZ2010/000083, filed Apr. 29, 2010, which claims priority from U.S. Provisional No. 61/173,656, filed Apr. 29, 2009.

BACKGROUND OF THE INVENTION

1. Field of the Invention

This invention relates to a gases supply and gases humidification apparatus, particularly but not solely for providing respiratory assistance to patients or users who require a supply of gas at positive pressure for the treatment of diseases such as Obstructive Sleep Apnea (OSA), snoring, or Chronic Obstructive Pulmonary Disease (COPD) and the like. In particular, this invention relates to a compressor or blower for use in a gases supply apparatus which in use is integral with the gases supply apparatus.

2. Description of the Related Art

Devices or systems for providing a humidified gases flow to a patient for therapeutic purposes are well known in the art. Systems for providing therapy of this type, for example CPAP therapy, have a structure where gases at the required pressure are delivered from a blower (also known as a compressor, an assisted breathing unit, a fan unit, a flow generator or a pressure generator) to a humidifier chamber downstream from the blower. As the gases are passed through the heated, humidified air in the humidifier chamber, they become saturated with water vapour. The gases are then delivered to a user or patient downstream from the humidifier, via a gases conduit.

Humidified gases can be delivered to a user from a modular system that has been assembled from separate units (that is, a system where the humidifier chamber/heater and the breathing unit/blower are separate items) connected in series via conduits. A schematic view of a user 1 receiving air from a known (prior art) modular assisted breathing unit and humidifier system is shown in FIG. 1. Pressurised air is provided from an assisted breathing unit or blower 2a via a connector conduit 10 to a humidifier chamber 4a. Humidified, heated and pressurised gases exit the humidifier chamber 4a via a user conduit 3, and are provided to the patient or user 1 via a user interface 5.

It is becoming more common for integrated blower/humidifier systems to be used. A typical integrated system consists of a main blower or assisted breathing unit which provides a pressurised gases flow, and a humidifier unit that mates with or is otherwise rigidly connected to the blower unit. This mating occurs for example by a slide-on or push connection, so that the humidifier is held firmly in place on the main blower unit. A schematic view of the user 1 receiving air from a known, prior art integrated blower/humidifier unit 6 is shown in FIG. 2. The system operates in the same manner as the modular system shown in FIG. 1, except that humidifier chamber 4b has been integrated with the blower unit to form the integrated unit 6.

The user interface 5 shown in FIGS. 1 and 2 is a nasal mask, covering the nose of the user 1. However, it should be noted that in systems of these types, a mask that covers both the mouth and nose, a full face mask, a nasal cannula, or any other suitable user interface could be substituted for the nasal mask shown. A mouth-only interface or oral mask could also be used. Also, the patient or user end of the conduit can be connected to a tracheostomy fitting, or an endotracheal intubation.

U.S. Pat. No. 7,111,624 includes a detailed description of an integrated system. A 'slide-on' water chamber is connected to a blower unit in use. A variation of this design is a slide-on or clip-on design where the chamber is enclosed inside a portion of the integrated unit in use. An example of this type of design is shown in WO 2004/112873, which describes a blower, or flow generator 50, and an associated humidifier 150.

For these systems, the most common mode of operation is as follows: air is drawn by the blower through an inlet into the casing which surrounds and encloses at least the blower portion of the system. The blower pressurises the air stream from the flow generator outlet and passes this into the humidifier chamber. The air stream is heated and humidified in the humidifier chamber, and exits the humidifier chamber via an outlet. A flexible hose or conduit is connected either directly or indirectly to the humidifier outlet, and the heated, humidified gases are passed to a user via the conduit. This is shown schematically in FIG. 2.

Impeller type fans or blowers are most commonly used in breathing systems of this type. An impeller blade unit is contained within an impeller housing. The impeller blade unit is connected to a drive of some form by a central spindle. A typical impeller housing is shown in FIGS. 3 and 4. A typical rotating impeller blade unit which in use is located inside the housing is shown in FIGS. 5 and 6. Air is drawn into the centre of the impeller unit through an aperture, and is then forced outwards from the centre of the housing towards an exit passage (usually located to one side of the housing) by the blades of the rotating impeller unit. An impeller blower suitable for use with a breathing system is described in U.S. Pat. No. 6,881,033.

Generally, domestic users receive treatment for sleep apnea or similar. It is most common for a nasal mask, or a mask that covers both the mouth and nose, to be used. If a nasal mask is used, it is common to strap or tape the mouth closed, so that the use of the system is effective (mouth leak and the associated pressure drop are substantially reduced or eliminated). For the range of flows dictated by the user's breathing, the CPAP device pressure generator provides a flow of gases at a substantially constant pressure. The pressure can usually be adjusted before use, or during use, either by a user, or a medical professional who sets up the system. Systems that provide variable pressure during use are also known—for example BiPAP machines that provide two levels of pressure: One for inhalation (IPAP) and a lower pressure during the exhalation phase (EPAP).

A person using a breathing assistance apparatus will inhale and exhale as part of their breathing cycle. As the user exhales, they are exhaling against the incoming gases stream provided by the blower. It is well-known in this field of technology to add a one-way or bias valve to the system, on or close to the mask or interface. A mask vent is described in U.S. Pat. No. 6,662,803. This allows exhaled air to be vented to atmosphere.

A mask vent of different design is described in EP 1275412.

U.S. Pat. No. 6,123,074 discloses a system where the mask includes an exhaust port, and where pressure in the breathing system is constantly monitored and a pressure controller downstream of the flow generator (between the mask and the flow generator) acts to maintain a constant pressure within the conduit.

U.S. Pat. No. 6,526,974 discloses a CPAP device where the size of the inlet to the blower or flow generator can be varied, or where the size of the inlet is automatically varied, in response to the needs of the user. An exhalation path is also provided.

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner.

SUMMARY OF THE INVENTION

It is an object of the present invention to provide a breathing assistance apparatus which goes some way to overcoming the abovementioned disadvantages or which at least provides the public or industry with a useful choice.

Accordingly, the invention may broadly be said to consist in a fan unit which in use forms part of a gases supply unit suitable for use as part of a system for providing heated gases to a user, the fan unit comprising: a casing defining a diffuser section, a volute, an inlet aperture and an outlet, the volute further defined by a channel that encircles the diffuser, the outlet having an exit aperture; an impeller located within the casing adapted for connection to a motor to drive rotation of the impeller about an axis when in use, the diffuser located at least partially annular around the impeller, the impeller further having an inducer adapted to receive a gases stream from the inlet aperture and an exducer to expel the gases supply to the diffuser and the volute; a passage providing fluid connection between an area proximate the exducer and an area proximate the inducer; wherein a lower surface of the diffuser and an inner wall of the channel define an angular transition of more than 270 degrees.

In another aspect, the invention may be said to consist in a fan unit which in use forms part of a gases supply unit suitable for use as part of a system for providing heated gases to a user, the fan unit comprising: a casing defining a diffuser section, a volute, an inlet aperture and an outlet passage, the outlet passage including an exit aperture; an impeller located within the casing adapted for connection to a motor to drive rotation of the impeller about an axis when in use, the impeller having the diffuser located annular thereto, the diffuser centred about the axis, the volute defined by a channel having an enlarging internal area and encircling the diffuser about the axis, the impeller having an inducer adapted to receive a gases supply from the inlet aperture and an exducer to expel the gases stream to the diffuser and the volute; a passage providing fluid connection between an area proximate the exducer and an area proximate the inducer; wherein the impeller has a surface at least partially sloped in an axial direction.

In another aspect, the invention may broadly be said to consist in a fan unit which in use forms part of a gases supply unit suitable for use as part of a system for providing heated gases to a user, the fan unit comprising: a casing defining a diffuser section, a volute, an inlet aperture and an outlet passage, the outlet passage including an exit aperture; an impeller located within the casing adapted for connection to a motor to drive rotation of the impeller about an axis when in use, the impeller having the diffuser located annular thereto, the diffuser centred about the axis, the volute defined by a channel having an enlarging internal area and encircling the diffuser about the axis, the impeller having an inducer adapted to receive a gases supply from the inlet aperture and an exducer to expel the gases stream to the diffuser and the volute; a passage providing fluid connection between an area proximate the exducer and an area proximate the inducer; wherein the airflow leaving the impeller is directed at least partially in an axial direction.

In another aspect, the invention may broadly be said to consist in a fan unit which in use forms part of a gases supply unit suitable for use as part of a system for providing heated gases to a user, said fan unit comprising: a casing defining a diffuser, a volute, an inlet and an outlet, said volute further defined by a channel that encircles said diffuser; an impeller located within said casing and adapted for connection to a motor, said impeller further having an inducer adapted to receive a gases stream from said casing inlet, said diffuser located at least partially annular to said impeller, said impeller further having an exducer adapted to expel gases to said diffuser and said volute; a passage providing a gases flow path between an area proximate said exducer and an area proximate said inducer; wherein a lower surface of said diffuser and an inner wall of said volute define an angular transition of more than 270 degrees.

In another aspect, the invention may broadly be said to consist in a fan unit which in use forms part of a gases supply unit suitable for use as part of a system for providing heated gases to a user, said fan unit comprising: a casing defining a diffuser, a volute, an inlet and an outlet, said volute further defined by a channel that encircles said diffuser; an impeller located within said casing and adapted for connection to a motor to rotate about an impeller axis, said impeller further having an inducer adapted to receive a gases stream from said casing inlet, said diffuser located at least partially annular to said impeller, said impeller further having an exducer adapted to expel gases to said diffuser and said volute; a passage providing a gases flow path between an area proximate said exducer and an area proximate said inducer; wherein airflow leaving said impeller is directed in a direction that is acute relative to the impeller axis and toward the entry of said passage.

In another aspect, the invention may broadly be said to consist in a fan unit which in use forms part of a gases supply unit suitable for use as part of a system for providing heated gases to a user, said fan unit comprising: a casing defining a diffuser, a volute, an inlet and an outlet, said volute further defined by a channel having a radially expanding volume that surrounds said diffuser; an impeller located within said casing and adapted for connection to a motor to rotate about an impeller axis; said impeller further having at least one gases flow path entry to receive gases from said casing inlet and a gases flow path exit to expel gases to said diffuser, said volute and said casing outlet; a passage providing a gases flow path from an area proximate said impeller gases flow path exit to at least one said impeller gases flow path entry; wherein gases passed through said impeller are directed in a direction that is acute relative to the impeller axis and toward the entry of said passage.

Preferably the inner surface of the casing is arched from an outer wall to an upper wall.

Preferably the angular transition is not more than 276 degrees.

Preferably the impeller has a plurality of blades capped by a lid.

Preferably the lid has a central aperture to provide an inlet to the impeller and thereby define an inlet flow path.

Preferably the channel is defined by an air gap between the lid and the casing.

Preferably the channel has an internal area enlarging in a radial direction.

Preferably the channel downwardly encircles the diffuser.

Preferably the lower surface of the diffuser is a separable member.

Preferably the separable member is a ring that at least partially encircles the impeller.

Preferably the lower surface of the diffuser is sloped up to 6 degrees from a plane tangential to the axis of impeller rotation.

Preferably the fan unit is part of a medical breathing assistance system.

Preferably the medical breathing assistance system is connectable to a patient to provide pressurised breathing gases.

Preferably the casing outlet is connectable to a humidification chamber.

Preferably fan unit comprises a plurality of blades, the blades extending at least partially in a direction of impeller rotation.

In another aspect, the invention may broadly be said to consist in a fan unit which in use forms part of a gases supply unit suitable for use as part of a system for providing heated gases to a user, said fan unit comprising: a casing defining a diffuser, a volute, an inlet and an outlet, said volute further defined by a channel that encircles said diffuser; an impeller located within said casing and adapted for connection to a motor, said impeller further having an inducer adapted to receive a gases stream from said casing inlet, said diffuser located at least partially annular to said impeller, said impeller further having an exducer adapted to expel gases to said diffuser and said volute; a passage providing a gases flow path between an area proximate said exducer and an area proximate said inducer; wherein airflow leaving said impeller is directed at least partially in an upwardly axial direction.

In another aspect, the invention may broadly be said to consist in a breathing assistance apparatus for providing heated gases to a patient, said apparatus unit comprising: a casing defining a diffuser, a volute, an inlet and an outlet, said volute defined by a channel internal to said casing that encircles said diffuser; an impeller located within said casing and adapted for connection to a motor, said impeller having an inducer adapted to receive a gases stream from said casing inlet, said diffuser located at least partially annular to said impeller, said impeller further having an exducer adapted to expel gases to said diffuser and said volute; a passage providing a gases flow path between an area proximate said exducer and an area proximate said inducer; wherein airflow leaving said impeller is directed at least partially in an upwardly axial direction.

Preferably the airflow leaving the impeller is directed by lower surface of the diffuser.

Preferably the airflow leaving the impeller is directed by the lower surface of the impeller exducer.

Preferably the airflow leaving the impeller is directed by a contour in the lower surface of the exducer, the contour continuing at least partially along the diffuser surface.

Preferably an inner surface of the casing is arched from an outer wall to an upper wall.

Preferably the impeller has a plurality of blades capped by a lid.

Preferably the lid has a central aperture to provide an inlet to the impeller and thereby define an inlet flow path.

Preferably the channel is defined by an air gap between the lid and the casing.

Preferably the channel has an internal area enlarging in a radial direction.

Preferably the channel downwardly encircles the diffuser.

Preferably the lower surface of the diffuser is a separable member.

Preferably the separable member is a ring that at least partially encircles the impeller.

Preferably the fan unit is part of a medical breathing assistance system.

Preferably the medical breathing assistance system is connectable to a patient to provide pressurised breathing gases.

Preferably the casing outlet is connectable to a humidification chamber.

Preferably the impeller comprises a plurality of blades, the blades extending at least partially in a direction of impeller rotation.

Preferably the airflow leaving the impeller is directed by lower surface of the diffuser.

Preferably the airflow leaving the impeller is directed by the lower surface of the impeller exducer.

Preferably the airflow leaving the impeller is directed by a contour in the lower surface of the exducer, the contour continuing at least partially along the diffuser surface.

Preferably the casing outlet is connectable to a patient to provide pressurised breathing gases.

Preferably the casing outlet is connectable to a humidification chamber.

Preferably a lower surface of the diffuser directs airflow leaving said impeller is directed in a direction that is acute relative to the impeller axis and toward the entry of said passage.

Preferably a lower surface of said impeller and a lower surface of the diffuser directs airflow leaving said impeller in a direction that is acute relative to the impeller axis and toward the entry of the passage.

Preferably a lower surface of the impeller directs airflow leaving said impeller in a direction that is acute relative to the impeller axis and toward the entry of said passage.

Preferably said impeller has a plurality of blades capped by a lid, the lid having a central aperture to provide an inlet to the impeller.

Preferably said channel has an internal area enlarging in a radial direction and downwardly encircling said diffuser.

Preferably said fan unit is part of a medical breathing assistance system that is connectable to a patient to provide pressurised breathing gases.

Preferably the impeller comprises a plurality of blades, the blades extending at least partially in a direction of impeller rotation.

Preferably the fan unit is part of a breathing assistance apparatus for providing heated gases to a patient.

Preferably the casing outlet is connectable to a patient to provide pressurised breathing gases.

Preferably the casing outlet is connectable to a humidification chamber.

This invention may also be said broadly to consist in the parts, elements and features referred to or indicated in the specification of the application, individually or collectively, and any or all combinations of any two or more of said parts, elements or features, and where specific integers are mentioned herein which have known equivalents in the art to which this invention relates, such known equivalents are deemed to be incorporated herein as if individually set forth.

BRIEF DESCRIPTION OF THE DRAWINGS

A preferred form of the present invention will now be described with reference to the accompanying drawings.

FIG. 7 shows an integrated blower/humidifier which forms part of the present invention, or which the present invention can be used with.

DETAILED DESCRIPTION OF THE PREFERRED EMBODIMENT

The present invention will be described with reference to a system where the humidifier chamber is integrated with the gases supply unit (also referred to as a respirator unit or blower unit). However, it should be noted that the system is equally applicable to a modular system.

Figure 1:
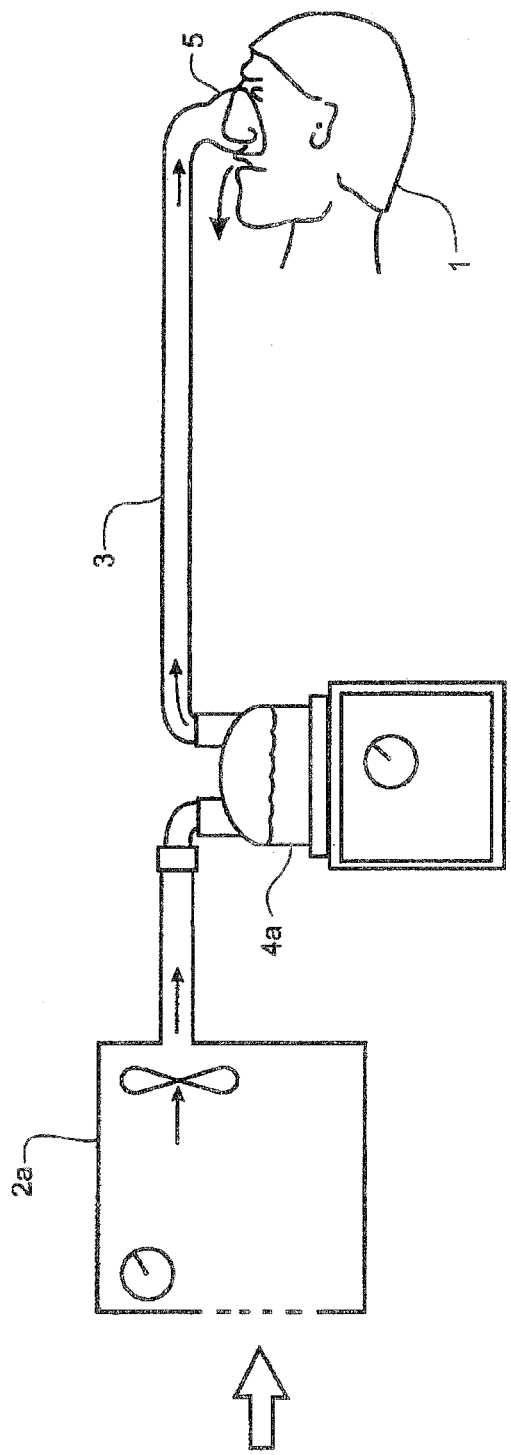
FIG. 1 shows a schematic view of a user receiving humidified air from a modular blower/humidifier system of a known, prior art, type.
Figure 2:
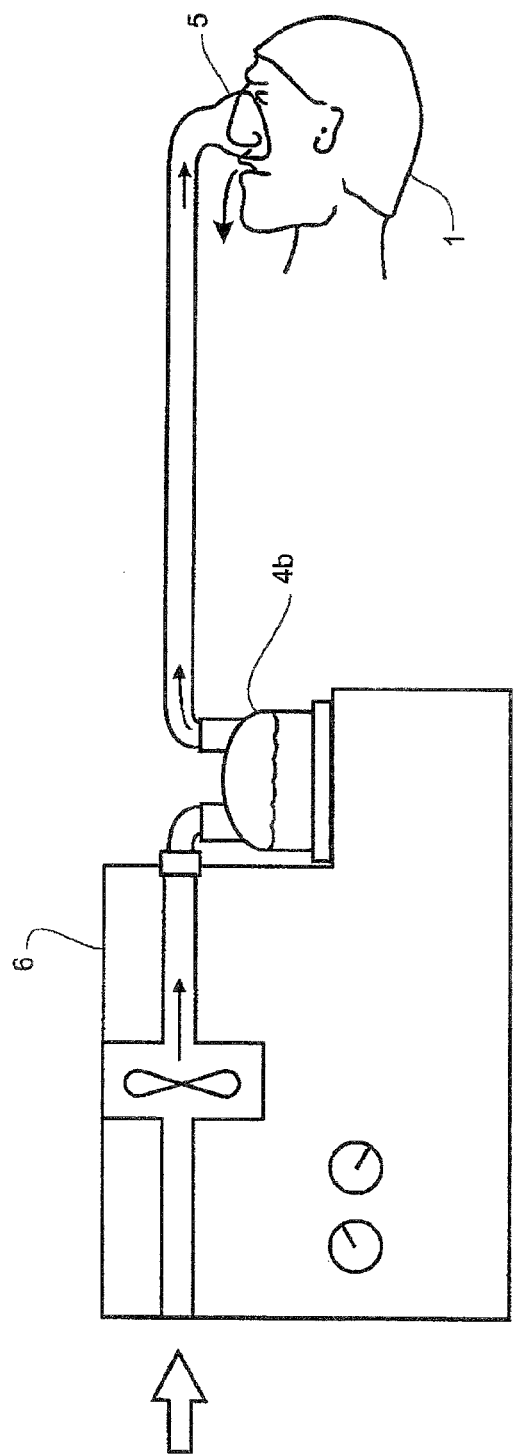
FIG. 2 shows a schematic view of a user receiving humidified air from an integrated blower/humidifier system of a known, prior art, type.
Figure 3:
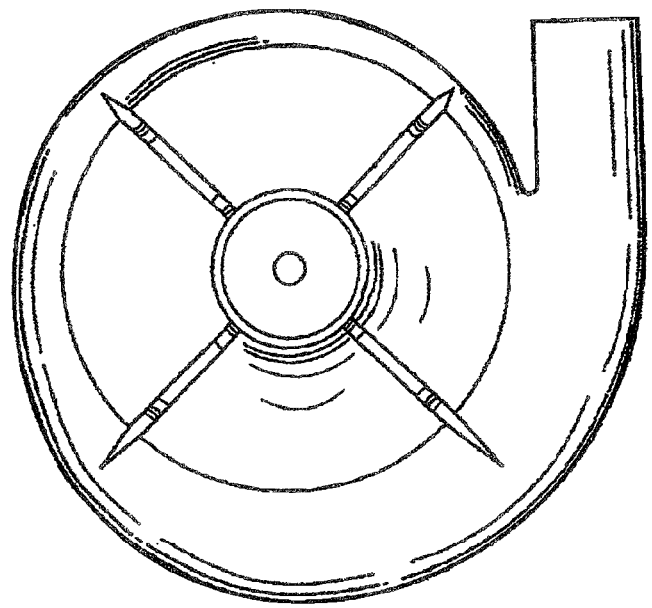
FIG. 3 shows a top view of an impeller casing or fan housing of a known, prior art, type which can be used with the blower or integrated blower/humidifier of FIGS. 1 and 2.
Figure 4:
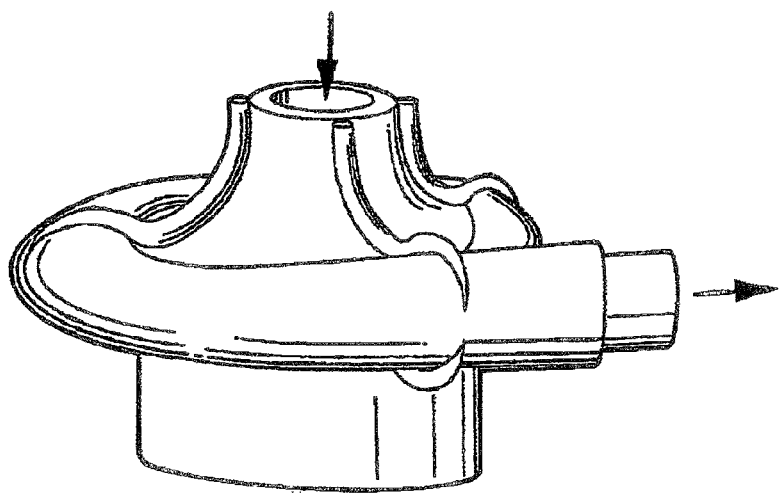
FIG. 4 shows a side view of the fan housing of FIG. 3.
Figure 5:
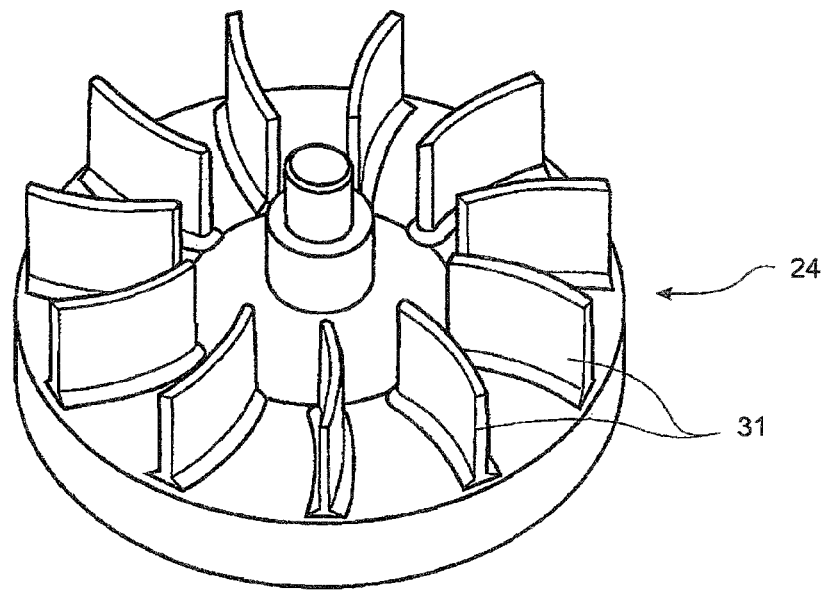
FIG. 5 shows a top perspective view of an impeller unit such as might be used as part of the fan of FIGS. 3 and 4.
Figure 6:
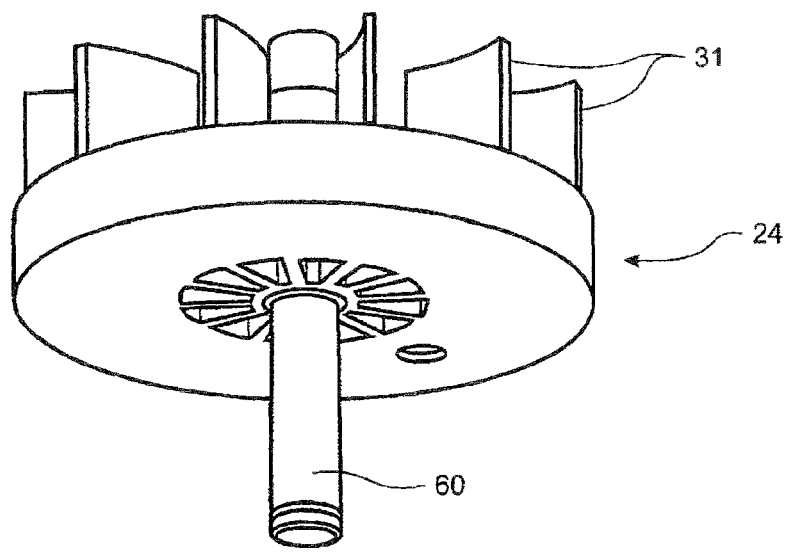
FIG. 6 shows a bottom perspective view of an impeller unit such as might be used as part of the fan of FIGS. 3 and 4.
Figure 7:
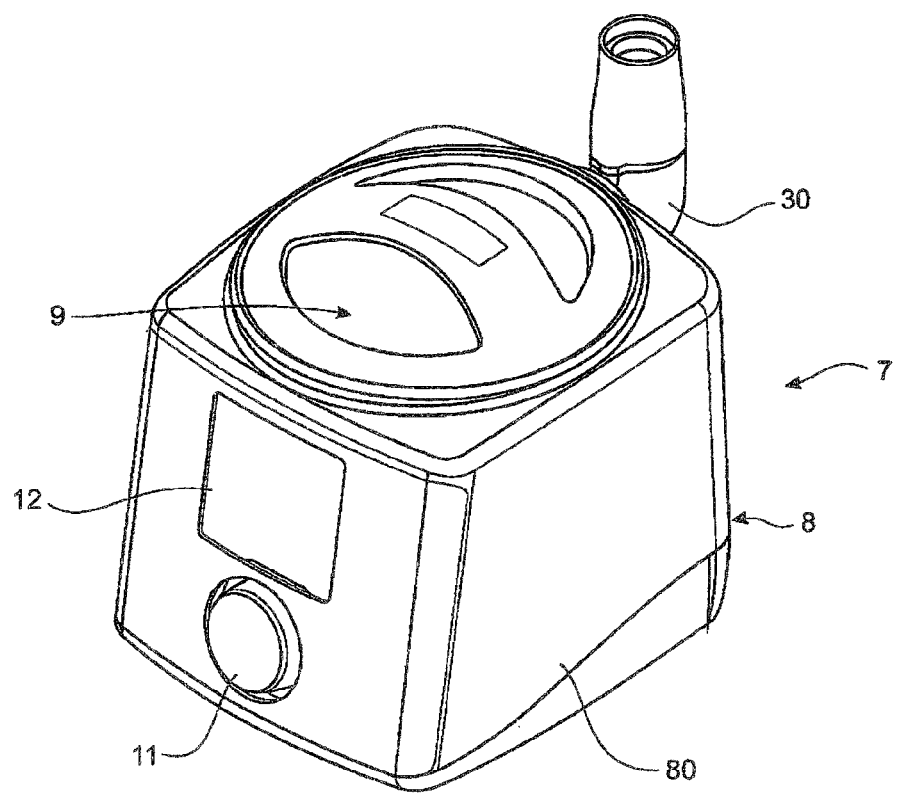

An integrated gases supply unit 7 with which the present invention can be used is shown in FIG. 7. The integrated unit 7 comprises two main parts: a gases supply unit or blower unit 8 and a humidifier unit 9. Humidification unit 9 is partially enclosed within the external shell 80 of the blower unit 8 in use, except for the top of the humidification unit 9.

The body of the gases supply unit 8 has the form of a generally rectangular block with substantially vertical side and rear walls, and a front face that is angled slightly rearwards (all the walls can be angled inwards slightly if required). In the preferred embodiment, the walls, base and top surface are all manufactured and connected as far as possible to minimise the occurrence of seams, and any necessary seams are sealed. As shown in FIG. 7, the gases supply unit 8 includes a control knob 11, located on the lower section of the front face of the gases supply unit 8, with a control display 12 located directly above the knob 11. A patient outlet 30 is shown passing out of the rear wall of the gases supply unit 8. In the preferred embodiment, the free end of the outlet 30 faces upwards for ease of connection. The patient outlet 30 is adapted to allow both pneumatic and electrical connection to one end of a conduit—e.g. conduit 3—running between the integrated unit 7 and a patient interface—e.g. interface 5. An example of the type of connector that can be used and the type of dual connection that can be made is described in U.S. Pat. No. 6,953,354. It should be noted that for the purposes of reading this specification, the patient interface can be thought of as including both the interface 5 and the conduit 3 where it would be appropriate to read it in this manner.

Figure 8:
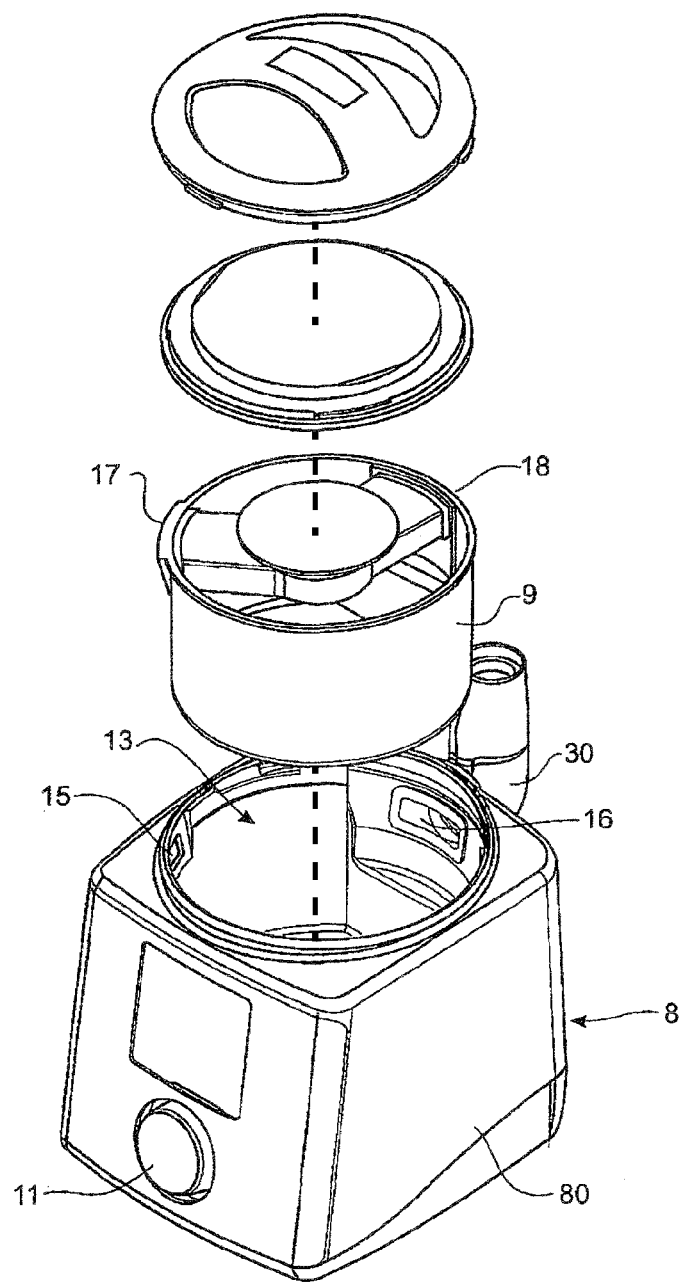
FIG. 8 shows an exploded view of the integrated blower/humidifier of FIG. 7.
Figure 9:
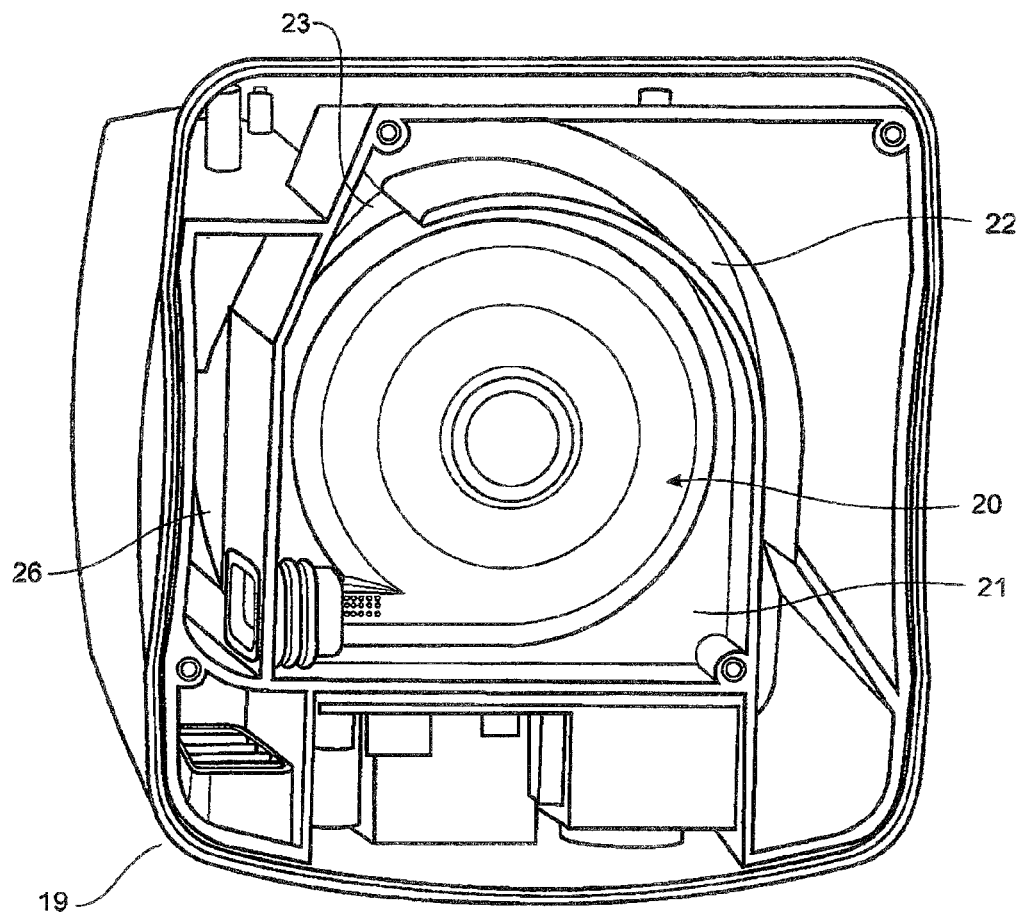
FIG. 9 shows a bottom perspective view of the blower of FIGS. 7 and 8.
Figure 10:
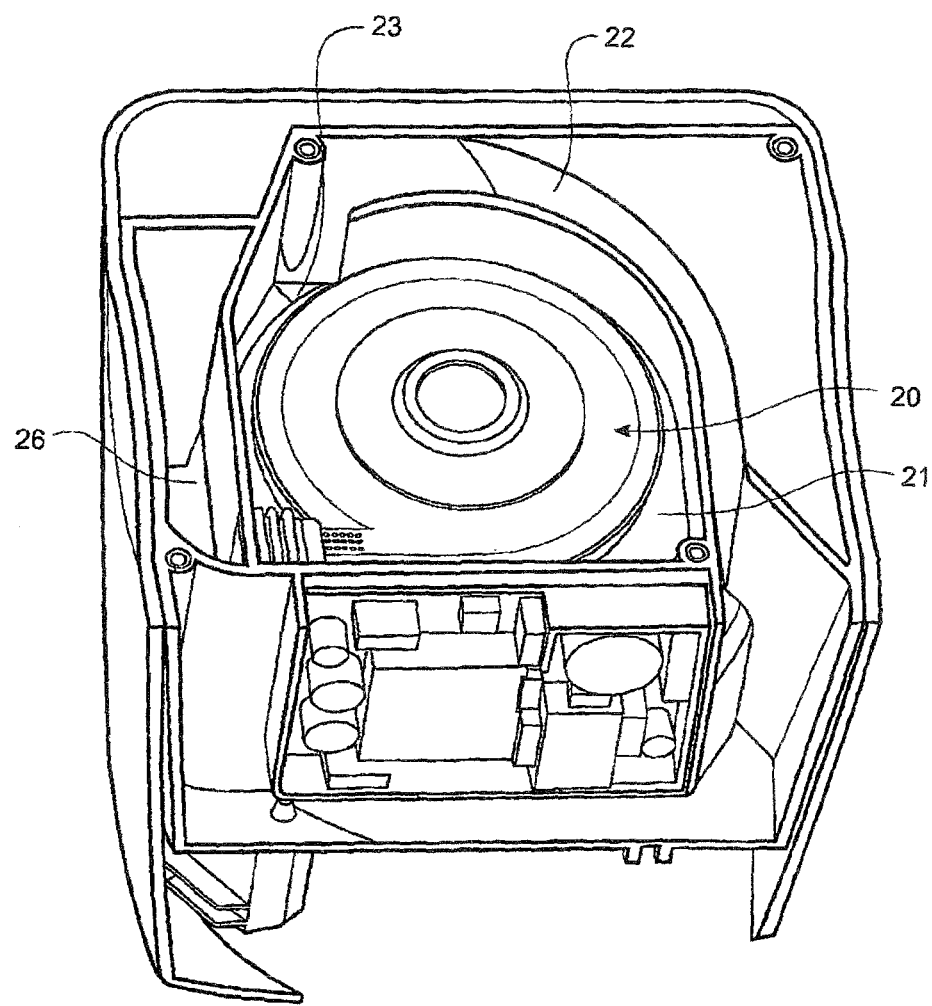
FIG. 10 shows a side bottom perspective view of the blower of FIGS. 7 and 8
Figure 11:
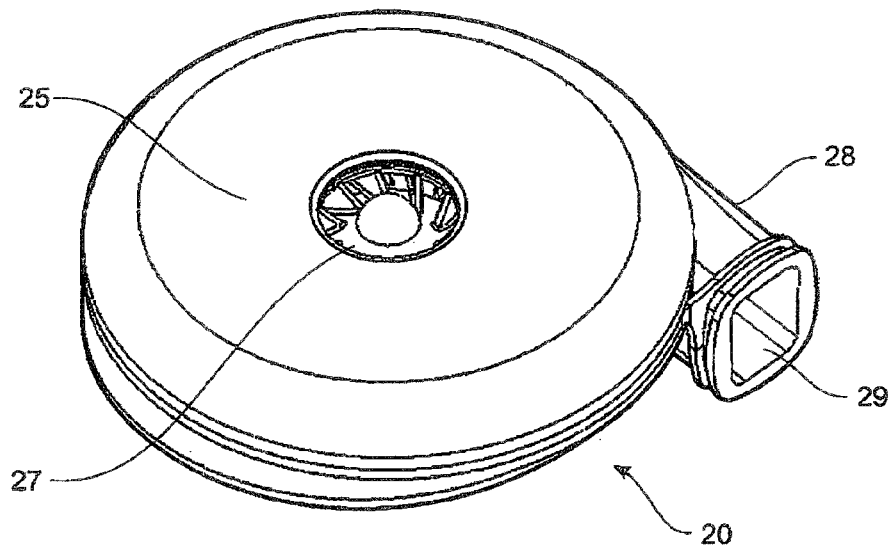
FIG. 11 shows a perspective top view of a fan casing for use with a system that provides heated, humidified air to a user, the casing having an inlet and an outlet passage.

The internal structure and components of the gases supply unit 8 will now be described with reference to FIGS. 8, 9 and 10. The gases supply unit 8 includes an enclosing external shell 80 which forms part of, and encloses, the gases supply unit 8. The shell 80 includes internal air passages for ducting air passing through the gases supply unit 8, and also internal recesses, cavities or slots into which componentry of the gases supply unit 8 is located in use. The shell 80 of the gases supply unit 8 is further adapted to include an open-topped compartment 13. In use, humidifier chamber 9 is located within the compartment 13. Blower unit 8 includes a heater base or heater plate (not shown), located at the bottom of the compartment 13. A humidifier inlet aperture 15 and humidifier outlet aperture 16 are located on the wall of the compartment 13, towards the top of the compartment 13. In the preferred embodiment, the inlet and outlet apertures 15, 16 are aligned so as to mate with inlet and outlet humidifier ports 17, 18 located on the humidifier chamber 9, when the system is in use. It should be noted that other forms of humidifier inlet are possible. For example a conduit running between the gases supply unit 8 and e.g. the lid of the humidifier chamber 9. Also, if the humidifier chamber is a separate item (that is, not rigidly connected to the gases supply unit in use), the humidifier inlet aperture 15 will not be connected directly to the humidifier chamber, but will be connected instead to one end of a conduit or similar leading from the humidifier inlet aperture on the gases supply unit, to the humidifier chamber.

Air from atmosphere is drawn into the shell of the gases supply unit 8 through an atmospheric inlet vent 19. This vent 19 can be located wherever is convenient on the external surface of the shell of the gases supply unit 8. In the preferred embodiment, as shown in FIG. 9, the inlet vent 19 is located on the rear face of the shell of the gases supply unit 8, on the right hand side of the rear face (right hand side when looking forwards). In the preferred embodiment, air is drawn in through the inlet vent 19 by means of a fan unit 20 which forms part of the gases supply unit 8, and which is located inside the enclosing external shell of the gases supply unit 8. The fan unit 20 provides a pressurised gases stream for the gases supply unit and therefore the assisted breathing system. The fan unit 20 will be described in more detail below. The air is drawn into the fan unit 20 indirectly, via a curved inlet path 22 formed through the shell of the gases supply unit 8. Path 22 runs from the inlet vent 19 to an aperture 23 formed in the gases supply unit shell 80, the aperture 23 passing into a recess 21 which is formed in the gases supply unit shell 80, in which the fan unit 20 is located.

The gases stream passes through the fan unit 20 to the humidifier inlet aperture 15 as follows: the shell of the gases supply unit 8 includes a chamber or outlet duct 26 which forms at least part of an outlet air path to allow gaseous communication between the fan unit 20 and the humidifier inlet aperture 15. In the preferred embodiment, the outlet duct 26 runs up between the right hand side wall of the gases supply unit 8 (from behind looking forwards) and the front wall, up to the humidifier inlet aperture 15. As shown in FIGS. 9 and 10, air exiting the fan unit 20 enters the duct 26.

In use, air exits the shell of the gases supply unit or blower 8 via the humidifier inlet aperture 15 and enters the humidifier chamber 9. In the preferred form, the humidifier inlet aperture 15 forms an outlet at the end of the duct 26. The gases are humidified and heated in the chamber 9, before passing out of the chamber 9 through the humidifier outlet aperture 16, which is directly or indirectly connected to the patient outlet 30 (it should be noted that the outlet of the humidifier chamber 9 could also be completely separate from the gases supply unit 8). The heated humidified gas is then passed to the user 1 via conduit 3. The patient outlet 30 is adapted to enable pneumatic attachment of the patient conduit 3, and in the preferred embodiment, outlet 30 is also adapted to enable electrical connection via an electrical connector. A combined electrical and pneumatic connection can be useful for example if the conduit 3 is to be heated. Electrical heating of a conduit such as conduit 3 can prevent or minimise the occurrence of condensation within the conduit 3. It should also be noted that the outlet connection does not have to be via the shell of the integrated unit 7. If required, the connection for the conduit 3 could be located directly on an outlet from humidifier chamber 9.

The blower unit 8 in use is set to a user-specified pressure level. The flow rate for the preferred embodiment will vary during use, depending on the users breathing. The power to fan unit 20 can be altered, to change the speed at which the impeller 24 is rotating, and therefore the pressure.

Figure 12:
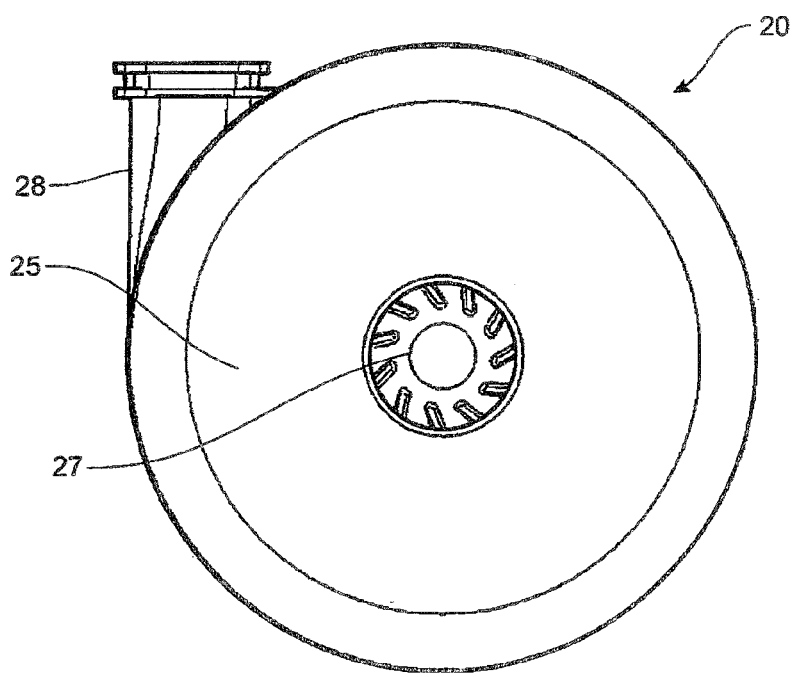
FIG. 12 shows a top view of the fan casing of FIG. 11.
Figure 13:
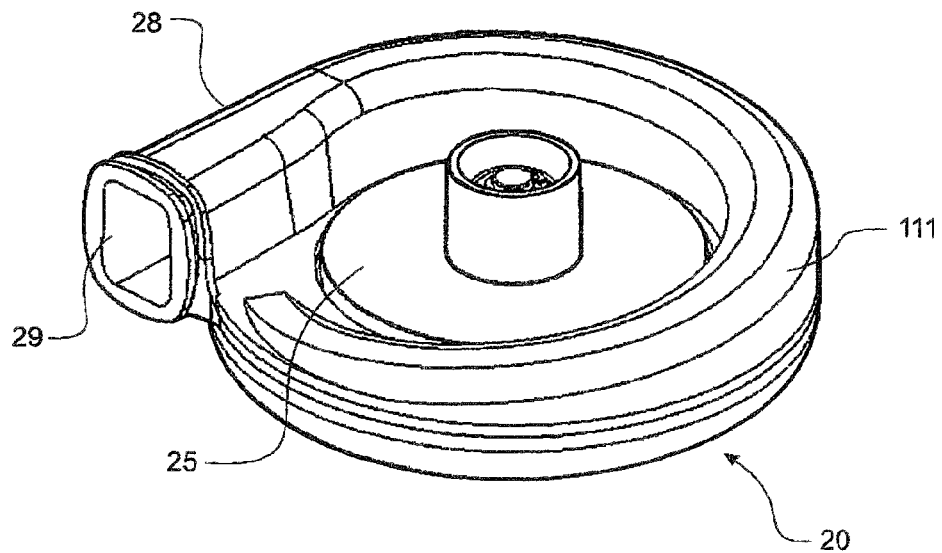
FIG. 13 shows a perspective bottom view of the fan casing of FIGS. 11 and 12.
Figure 14:
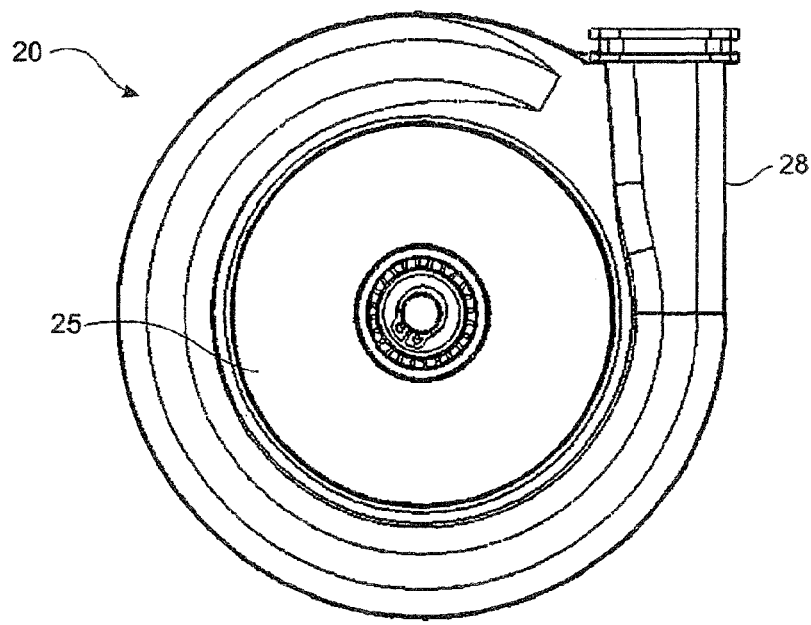
FIG. 14 shows a bottom view of the fan casing of FIGS. 11, 12 and 13.

The structure of the fan unit 20 shall now be described, with particular reference to FIGS. 11 to 16. The fan unit 20 is located in recess 21 of the shell of the gases supply unit 8 in use, as described above with reference to FIGS. 9 and 10. In the preferred form, the fan unit 20 comprises a rotating impeller unit 24 located inside a casing having the form of a snail or scroll casing 25. The compressor or fan located inside the casing 25 will be referred to in the general as a 'fan' for the purposes of this specification, and as 'impeller unit 24' for the specific preferred embodiment. It can be seen that the fan unit 20 appears generally circular in plan view, as shown in FIGS. 12 and 14. The fan casing 25 includes an inlet aperture 27. In the preferred form, inlet aperture 27 is a circular hole located in approximately the centre of the lower face of the casing 25 and passing from the outside of the casing to the inside. Air from the inlet path 22 enters the fan casing 25 via the inlet aperture 27. It should be noted that where it would be appropriate to include the aperture 23 and at least part of the recess 21 as part of the air inlet path, the specification should be read as including these elements. The preferred form of the casing 25 of the fan unit 20 also includes an outlet passage 28. In the preferred form, the outlet passage 28 is a short passage formed as an integral part of the casing 25 and aligned substantially circumferentially to the remainder of the generally circular casing 25. A fan casing outlet aperture or exit aperture 29 is located at the outer end of the passage 28. It should be noted that the fan casing exit aperture 29 could be located wherever is convenient on the passage 28 (i.e. it does not have to be at the end of the passage, it could be through the passage wall partway along its length). Exit aperture 29 opens into the duct 26.

The outlet passage 28 forms part of the air path from the fan to the humidifier inlet aperture 15. The fan casing 25 encloses the fan in use, except for the inlet aperture 27 and the exit aperture 29 of the passage 28.

In the preferred embodiment, rotation of the fan unit 20 is driven by a motor (not shown) located outside the casing 25, the fan or impeller unit 24 being adapted for connection to the motor. In the preferred embodiment, the motor is located below the casing 25 in the recess 21, and is an electromagnetic motor. Impeller unit 24 includes a spindle 60 which passes vertically downwards out of the casing 25 to connect with the motor. In use, the motor is powered to rotate the spindle, which causes rotation of the impeller unit 24. In alternative embodiments, the fan could be run indirectly by the motor, for example by gears or similar connecting the fan to the motor, or by magnetic induction or similar. Air or gases are drawn through inlet aperture 27 in the centre of the casing 25, into the centre of the impeller unit 24, and are then forced outwards as a gases stream through the exit aperture 29 of the outlet passage 28 by the impeller blades 31 as the impeller unit 24 rotates.

In the preferred form, the fan outlet passage or exit passage 28 is aligned substantially tangentially to the casing 25. The cross-section of the fan outlet passage 28 could be any suitable shape, such as oval, rectangular or circular. The fan outlet passage 28 causes the gases forced outwards by the impeller unit 24 to coalesce as a fluidic gases stream, and dictates the direction in which the gases stream flows. There will inevitably be some swirling of the gases within the passage. However, the coarse path or overall direction of the gases flow will be along the passage from the fan towards the fan casing exit aperture 29.

A person using a breathing assistance apparatus will inhale and exhale as part of their breathing cycle. As the user exhales, they are exhaling against the incoming gases stream provided by the blower, thereby increasing the pressure in the conduit 3 and throttling the gases stream flow. The pressure increase can cause the flow through an impeller to abruptly decelerate or reverse, in turn causing the impeller to stall or surge. Stall or surge can result in high frequency fluctuations in the pressure of the delivered gases stream. The fluctuations can be felt by the user through the gases stream and can cause audible noise, both of which are disturbing for a user. The fluctuations can also introduce vibration into mechanical structures of the system that can cause additional noise that is disturbing for a user.

It has been found that the addition of a gasses recirculation passage in the fan unit 20 goes some way toward preventing the onset of stall or surge. The recirculation passage allows for the gasses stream exiting the impeller to be recirculated to the input of the impeller in a general flow direction opposite to that of the main flow. The recirculation passage allows the onset of surge or stall to be displaced in favour of lower mass air flow at the output of the fan unit 20. For example, as the user exhales during a normal part of their breathing cycle, the mass air flow through the impeller 24 drops due to the pressure increase seen at the output of the blower.

The recirculation passage maintains the air flow rate through the impeller to avoid flow instability and the associated side effects, while also maintaining a desired output pressure. The useful operating range of the impeller is therefore increased. A preferred form of gases recirculation passage will now be described with particular reference to FIG. 15.

Figure 15:
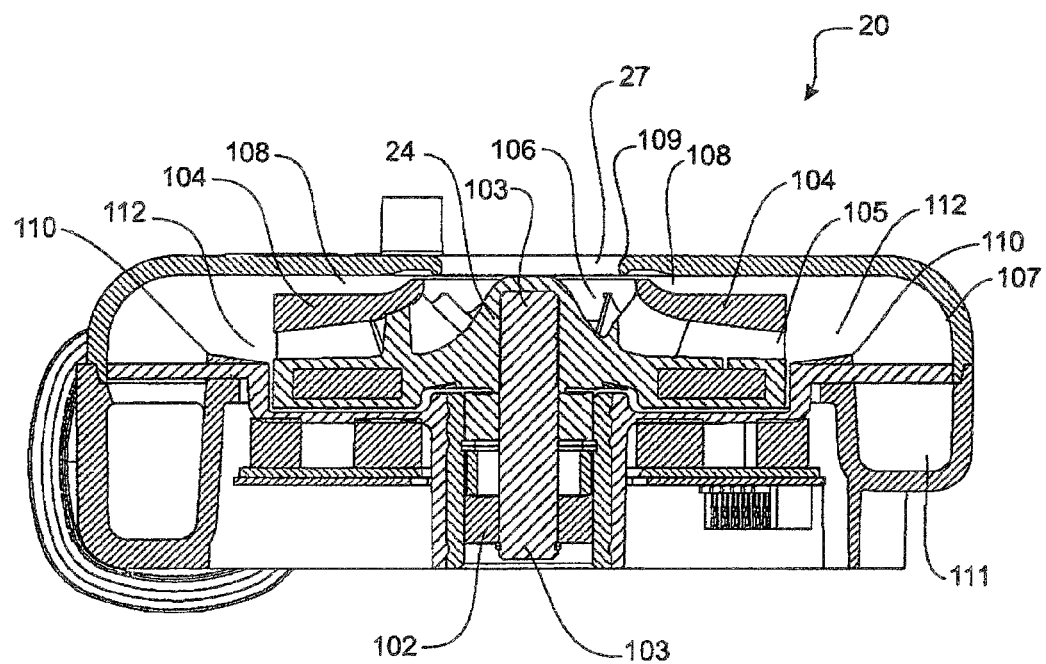
FIG. 15 shows a cross sectional view of the fan casing of the preferred embodiment, with an impeller in place.

FIG. 15 shows a cross-sectional drawing of the blower unit 20. A motor 102 drives a central shaft 103 that is connected to the impeller 24. Preferably the motor 102 is electrically driven, such as by a brushless DC motor. When the motor 102 is energised, the impeller 24 is rotated to cause air to be drawn through the inlet aperture 27. A guide member 104 located immediately above and annular to the impeller 24 ensures air drawn into the blower 20 is guided between the impeller inlet and outlet. In this specification, the portion of the impeller where airflow enters is known as the inducer 106, and the portion of the impeller where airflow exits the impeller is known as the exducer 105. The guide member 104 may in alternative forms be replaced with an integral surface to seal the impeller vanes. The preferred form of recirculation passage 108 is shown fluidly connecting the gas flow paths proximate the exducer 105 and inducer 106 of the impeller. It should be noted that the recirculation passage 108 may be constructed to allow the gasses stream to enter from any location down stream of the impeller exducer 105. The up stream end (i.e. at or close to the inducer 106) of the recirculation passage 108 may include a lip 109 or contour to guide air flow toward the inducer 106 to ensure smooth integration of recirculated gases with gases entering the aperture 27.

The internal construction of the impeller casing 20 ideally includes a diffuser portion 112 and a volute 111. The diffuser 112 serves to decelerate the gas flow exiting the impeller thereby increasing static pressure. The general shape of the volute 111 is illustrated in FIG. 13 as an enlarging channel that encircles the impeller 24. The volute 111 collects the gas from the diffuser 112 and transports it to the outlet passage 28. During collection of the gas, the volute 111 further decelerates flow due to the enlarging cross sectional area to increase static pressure of the gas flow. The volute typically enlarges in a direction downward relative to the direction of airflow entering the impeller. Other language used in this specification to describe upward and downward directions is intended to refer to directions relative to the direction of airflow entering the impeller unless otherwise stated.

If excessive pressure is built up at the output passage 28, such as when the user exhales, gas flow from the diffuser 112 to the volute 111 is slowed, stopped, or even reversed. Under these conditions, air flow exiting the impeller 24 flows through the recirculation passage 108 as the passage becomes a 'path of least resistance'. In such circumstances, the velocity of the gas flow though the impeller is maintained, while flow at the output of the blower unit 20 is produced only when required by the user.

In the instance of flow build-up or reversion, when high enough pressure is generated by the user exhaling, the gases stream cannot exit the outlet passage 28 or even re-enters the volute 111 via the outlet passage 28. The gases stream in the diffuser 112 which has exited the impeller combines with the gases stream re-entering the volute at the adjoining edge of the volute and diffuser in a turbulent manner. The turbulence can lead to flow instability in the impeller and the diffuser 112, thereby reducing the effectiveness of the recirculation passage 108 and potentially resulting in unwanted impeller stall or surge. The adjoining edge is typically a 90° angular transition formed by the substantially horizontal plane of the diffuser and the inside wall of the volute channel. Typically, the angular transition formed by the adjoining edge of the diffuser and the volute entirely encircles the impeller. However, it is envisaged the angular transition may only partially encircle the impeller, for example, where additional vanes of airflow guide members are used inside the casing to alter airflow characteristics.

In the preferred embodiment of the invention, to avoid flow instability as a result of flow reversion, an annular ramp, a wedge member or an inclining surface 110 forms part of the construction of the fan unit 20. The ramp, wedge or surface is henceforth referred to as the wedge member 110. The wedge member 110 is arranged and sized to at least partially encircle the impeller exducer 105. The preferred wedge member 110 is shaped and orientated to direct the gasses stream exiting the impeller toward the top surface of the impeller casing 20, thereby creating a higher angle of incidence against the upper volute wall 107. The most preferred ramp angle of the wedge member 110, relative to the plane of gases exiting the impeller, is preferably not more than 6 degrees to avoid breakdown of air flow boundary layers in the diffuser that would further hinder flow stability. Directing the air flow in the diffuser 112 at least partially toward the direction of airflow re-entering the diffuser from the volute 111 provides smoother recombination of the two gas streams, thereby reducing turbulence. A curved inner wall 107 of the volute 111 also facilitates a smoother flow path toward the entry of the recirculation passage 108 by allowing the gas stream to follow a smoother contour that avoids any further turbulence that may hinder airflow.

The airflow exiting the impeller has tangential and radial components. The strength of these components is somewhat dependent on the contour of the impeller blades. For example, forward facing impeller blades impart a strong tangential velocity to the airflow. Whereas back facing blades impart a strong radial velocity to the airflow. In the preferred impeller, the blades are forward facing such that a strong tangential and reduced radial velocity components are imparted to the airflow leaving the impeller. In this way, the airflow is encouraged to tangentially swirl inside the diffuser 112 and volute 111. The reduced radial velocity component of the airflow provides a less turbulent transition around the adjoining edge of the diffuser 112 and volute 111 by directing airflow toward the top surface of the volute 107 before heading down the outer wall. The swirling also promotes smoother airflow into the recirculation passage 108. Swirling may also be promoted by positioning vanes in the diffuser to direct airflow in a radial direction.

Preferably the wedge member 110 is moulded into the impeller casing. However, it is envisaged the wedge may also be detachable to allow retro-fitment to the diffusers of existing blowers, or the ability to swap one of numerous ramp angles best suited to a particular user breathing profile.

Figure 16:
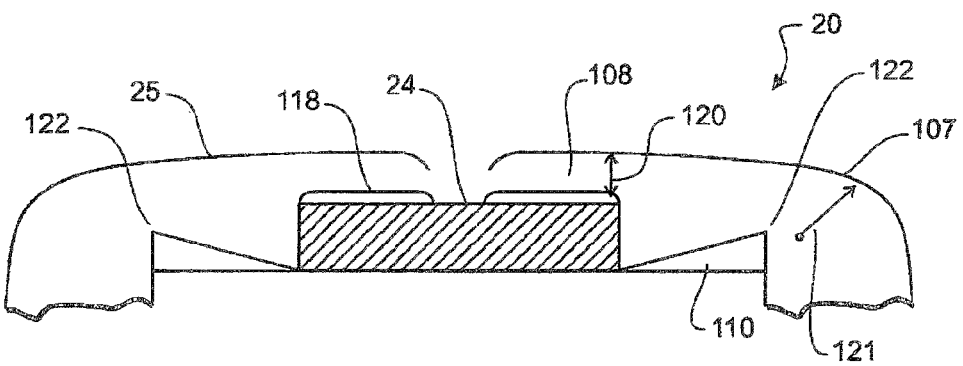
FIG. 16 shows a stylised cross sectional view of the fan casing and impeller of the preferred embodiment.

FIG. 16 shows an illustrative view of the impeller 24 inside the impeller housing 25. Preferably the inner wall of the housing 107 has a radius 121 as large as possible to promote smoother air flow to the recirculation passage 108. The recirculation passage has been found to operate successfully when 1 mm in height as shown by dimension 120. Enlarging the passage height 120 would promote more air flow recirculation, further promoting a reduction in potential air flow instability with the trade-off of reducing mass air flow rate obtainable at the output of the blower. It is further apparent that the recirculation passage 108 may comprise a series of passages. The collective area of the passages will define the rate of air flow recirculation.

The recirculation passage 108 may be defined by an aperture, or at least a fluid connection, formed in the blower housing 25 or separate structure. In the preferred embodiment, the impeller is formed with a 'lid' 118 to substantially enclose the vanes between the inducer 106 and exducer 105. An air gap above the lid will form the required recirculation passage 108 by allowing air to flow above the impeller 24 without impeding the airflow through the impeller vanes. Further, the recirculation passage may be formed by a fluid communication between any two points upstream, downstream or midstream relative to the impeller.

Preferably, the wedge member 110 is entirely annular and runs all the way around the impeller 24. However, a partially annular wedge has been found to also provide improved surge characteristics. Ramp angles of the wedge may be more or less than 6° to tune the most effective smoother airflow recombination angle at and around the angular transition 122, whereby steeper angles provide smooth recombination and shallower angles provide more turbulent recombination. The angular transition 122 extends radially around the exterior of the lower surface diffuser where it meets the volute 107. Typically the angular transition from the diffuser surface to the volute is an angle of 270 degrees. The addition of the wedge member 110 increases that angle. Increased ramp angles of the wedge member 110 may also be used to increase the rate of recirculation through the recirculation passage 108, albeit at the expense of increased noise levels. Lower ramp angles may be used to provide a reduction in airflow recirculation through the recirculation passage 108 and therefore a reduction in mass airflow and pressure.

In addition to the angle of the ramp, the channel area through the recirculation passage 108 can be enlarged to increase the amount of airflow recirculated, and therefore the mass airflow and pressure seen by the impeller. However, the recirculation passage volume can be enlarged to the point where too much airflow escapes back to the inducer 24. In such circumstances, a labyrinth seal in the recirculation passage could be used to reduce pressure loss.

Figure 17:
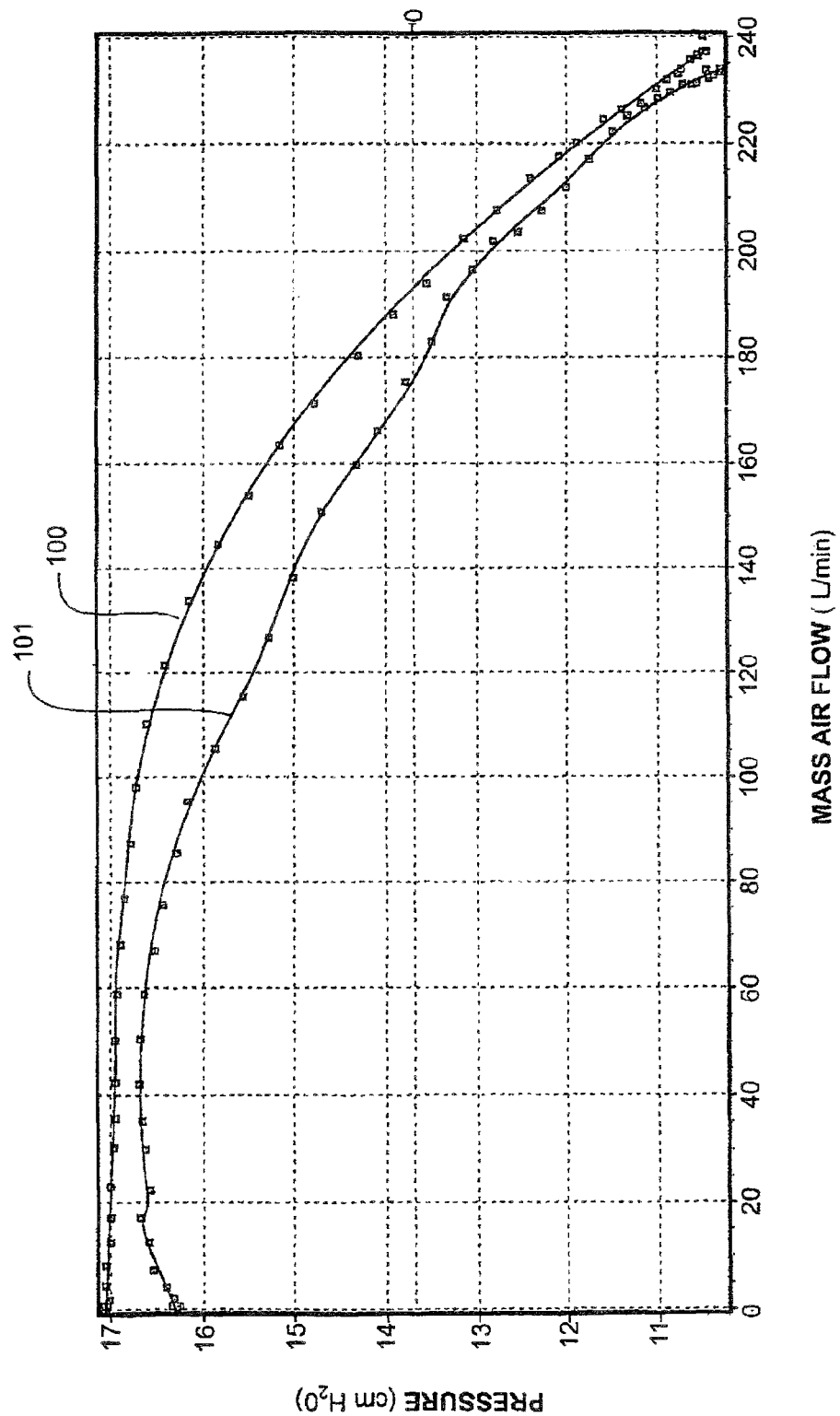
FIG. 17 shows a graph of airflow characteristics of the impeller and fan casing of the present invention over a range of operating conditions.
Figure 18:
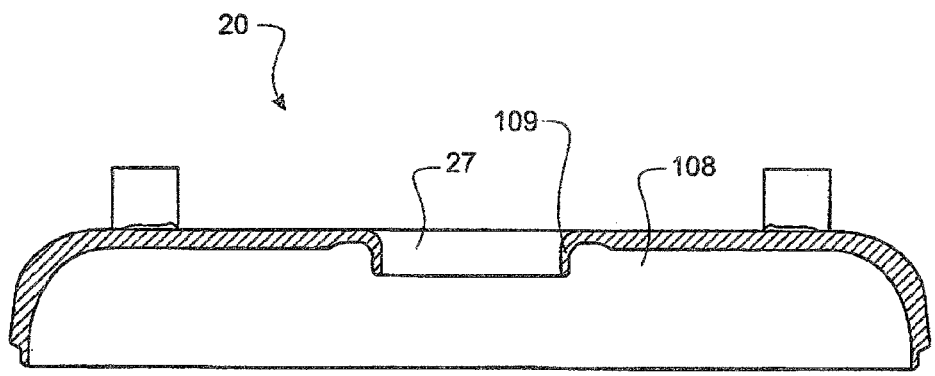
FIG. 18 shows a stylised cross sectional view of the impeller and diffuser the fan casing and impeller of an alternative embodiment.

FIG. 17 shows an experimental plot comparing mass air flow and pressure between blower configurations with and without the annular wedge 110. Line 101 shows a flow curve for a blower without the annular wedge. Line 100 shows a flow curve for the same blower while having the wedge member 110 in place. At high pressure and low mass flow rates (the area where flow instability is most likely to occur), it is apparent the addition of the wedge member 110 has increased the mass airflow. The improvement is particularly evident when the mass flow rate nears zero, such as when the user is exhaling.

Figure 19:
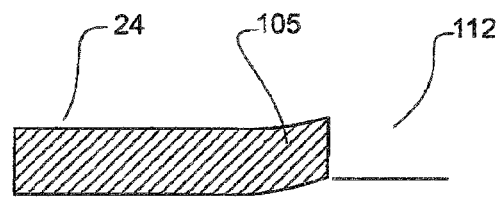
FIG. 19 shows a stylised cross sectional view of the impeller and diffuser of an alternative embodiment.
Figure 20:
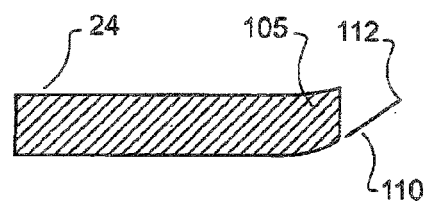
FIG. 20 shows a stylised cross sectional view of the impeller and diffuser of an alternative embodiment.

In an alternative embodiment of the present invention the impeller 24 has an exducer 105 formed to direct airflow leaving the impeller in an upward direction, or at least in the general direction of the entrance of the recirculation passage 108. Directing the airflow upward may be facilitated by forming the impeller by having at least part of the sealing lower surface sloping toward the ceiling of the diffuser, such as shown in FIG. 19. In this way, the flow of gas has an axial velocity component imparted to the airflow, and the wedge member 110 would not be required. It will also be apparent to those skilled in the art that alternative arrangements are possible. For example, a combination of the wedge member 110 and an upwardly sloped lower sealing surface of the impeller. FIG. 20 shows a cross sectional view of the impeller sloping upward at the exducer 105, and the wedge member 110 formed to continue the curvature of the exducer for some distance.

In the preferred form, the blower unit is set by a user to a constant pressure setting, which can be adjusted to different (constant pressure) levels according to the users needs. The flow rate delivered by the CPAP unit or blower unit 8 for any particular constant pressure setting is variable, and depends on an individual user's breathing pattern. Ideally, a CPAP device would deliver a constant pressure for all flow rates. However, in use, for any given pressure setting, the blower unit 8 will actually deliver a variable pressure and flow rate as a user breathes.

The preferred form of fan unit is speed adjustable, to provide a range of pressures preferably between approximately 4 cmH20 and 20 cmH20 for flow rates of up to 240 L/minute.

While preferred embodiments of the present invention are shown and described, it is envisioned that those skilled in the art may devise various modifications of the present invention without departing from the spirit and scope of the appended claims.

The invention claimed is:

1. A fan unit which in use forms part of a gases supply unit suitable for use as part of a system for providing heated gases to a user, said fan unit comprising:
   a casing defining a diffuser, a volute, an inlet and an outlet, said volute further defined by a channel that encircles said diffuser,
   an impeller located within said casing and adapted for connection to a motor, said impeller further having an inducer adapted to receive a gases stream from said casing inlet, said diffuser located at least partially annular to said impeller, said impeller further having an exducer adapted to expel gases to said diffuser and said volute,
   a recirculation passage providing a gases flow path between an area proximate said exducer and an area proximate said inducer,
   wherein a lower surface of said diffuser and an inner wall of said volute define an angular transition of more than 270 degrees,
   wherein said lower surface of the diffuser is sloped up to 6 degrees from a plane tangential to the axis of impeller rotation.

2. A fan unit as claimed in claim 1, wherein an inner surface of said casing is arched from an outer wall to an upper wall.

3. A fan unit as claimed in claim 1, wherein said impeller has a plurality of blades enclosed by a lid, said lid having an aperture to provide a gases inlet to said impeller.

4. A fan unit as claimed in claim 3, wherein said recirculation passage is defined by a gap between said lid and said casing.

5. A fan unit as claimed in claim 1, wherein said channel has an internal area enlarging in a radial direction.

6. A fan unit as claimed in claim 1, wherein said channel extends below the plane of the inducer.

7. A fan unit as claimed in claim 1, wherein the lower surface of said diffuser is a separable member.

8. A fan unit as claimed in claim 7, wherein said separable member is a ring that at least partially encircles said impeller proximate to said exducer.

9. A fan unit as claimed in claim 1, wherein said fan unit is part of a medical breathing assistance system connectable to a patient to provide pressurised breathing gases, wherein said casing outlet is connectable to a humidification chamber.

10. A fan unit as claimed in claim 1, wherein said impeller has a plurality of blades, said blades extending at least partially in a direction of impeller rotation.

11. A fan unit which in use forms part of a gases supply unit suitable for use as part of a system for providing heated gases to a user, said fan unit comprising:
   a casing defining a diffuser, a volute, an inlet and an outlet, said volute further defined by a channel that encircles said diffuser,
   an impeller located within said casing and adapted for connection to a motor to rotate about an impeller axis, said impeller further having an inducer adapted to receive a gases stream from said casing inlet, said diffuser located at least partially annular to said impeller, said impeller further having an exducer adapted to expel gases to said diffuser and said volute,
   a recirculation passage providing a gases flow path between an area proximate said exducer and an area proximate said inducer,
   wherein airflow leaving said impeller is directed in a direction that is acute relative to the impeller axis and toward the entry of said recirculation passage, wherein said impeller has a plurality of blades capped by a lid, said lid having a central aperture to provide an inlet to said impeller.

12. A fan unit as claimed in claim 11, wherein a lower surface of the diffuser directs airflow leaving said impeller in a direction that is acute relative to the impeller axis and toward the entry of said passage.

13. A fan unit as claimed in claim 11, wherein a lower surface of said impeller and a lower surface of the diffuser directs airflow leaving said impeller in a direction that is acute relative to the impeller axis and toward the entry of said passage.

14. A fan unit as claimed in claim 11, wherein a lower surface of said impeller directs airflow leaving said impeller in a direction that is acute relative to the impeller axis and toward the entry of said passage.

15. A fan unit as claimed in claim 11, wherein an inner surface of said casing is arched from an outer wall to an upper wall.

16. A fan unit as claimed in claim 11, wherein said recirculation passage is defined by an air gap between said lid and said casing.

17. A fan unit as claimed in claim 11, wherein said channel has an internal area enlarging in a radial direction and downwardly encircling said diffuser.

18. A fan unit as claimed in claim 11, wherein the lower surface of said diffuser is a separable member.

19. A fan unit as claimed in claim 18, wherein said separable member is a ring that at least partially encircles said impeller proximate said exducer.

20. A fan unit as claimed in claim 11, wherein said fan unit is part of a medical breathing assistance system that is connectable to a patient to provide pressurised breathing gases.

21. A fan unit as claimed in claim 11, wherein the impeller comprises a plurality of blades, said blades extending at least partially in a direction of impeller rotation.

22. A breathing assistance apparatus as claimed in claim 21, wherein said casing outlet is connectable to a humidification chamber.

23. A breathing assistance apparatus for providing heated gases to a patient, said apparatus including a fan unit having the features of claim 11.

24. A breathing assistance apparatus claimed in claim 23, wherein said casing outlet is connectable to a patient to provide pressurised breathing gases.

25. A fan unit which in use forms part of a gases supply unit suitable for use as part of a system for providing heated gases to a user, said fan unit comprising:
a casing defining a diffuser, a volute, an inlet and an outlet, said volute further defined by a channel having a radially expanding volume that surrounds said diffuser,
an impeller located within said casing and adapted for connection to a motor to rotate about an impeller axis, said impeller further having at least one gases flow path entry to receive gases from said casing inlet and a gases flow path exit to expel gases to said diffuser, said volute and said casing outlet,
a recirculation passage providing a gases flow path from an area proximate said impeller gases flow path exit to at least one said impeller gases flow path entry,
wherein gases passed through said impeller are directed in a direction that is acute relative to the impeller axis and toward the entry of said recirculation passage,
wherein said impeller has a plurality of blades capped by a lid, said lid having a central aperture to provide an inlet to said impeller.

26. A fan unit as claimed in claim 25, wherein a lower surface of the diffuser directs airflow leaving said impeller is directed in a direction that is acute relative to the impeller axis and toward the entry of said recirculation passage.

27. A fan unit as claimed in claim 25, wherein a lower surface of said impeller and a lower surface of the diffuser directs airflow leaving said impeller in a direction that is acute relative to the impeller axis and toward the entry of said recirculation passage.

28. A fan unit as claimed in claim 25, wherein a lower surface of said impeller directs airflow leaving said impeller in a direction that is acute relative to the impeller axis and toward the entry of said recirculation passage.

29. A fan unit as claimed in claim 25, wherein an inner surface of said casing is arched from an outer wall to an upper wall.

30. A fan unit as claimed in claim 25, wherein said recirculation passage is defined by an air gap between said lid and said casing.

31. A fan unit as claimed in claim 25, wherein said channel has an internal area enlarging in a radial direction and downwardly encircling said diffuser.

32. A fan unit as claimed in claim 25, wherein the lower surface of said diffuser is a separable member.

33. A fan unit as claimed in claim 32, wherein said separable member is a ring that at least partially encircles said impeller proximate said exducer.

34. A fan unit as claimed in claim 25, wherein said fan unit is part of a medical breathing assistance system that is connectable to a patient to provide pressurised breathing gases.

35. A fan unit as claimed in claim 25, wherein the impeller comprises a plurality of blades, said blades extending at least partially in a direction of impeller rotation.

36. A breathing assistance apparatus for providing heated gases to a patient, said apparatus including a fan unit having the features of claim 25.

37. A breathing assistance apparatus claimed in claim 36, wherein said casing outlet is connectable to a patient to provide pressurised breathing gases.

38. A breathing assistance apparatus as claimed in claim 36, wherein said casing outlet is connectable to a humidification chamber.

* * * * *